United States Patent [19]
Schleicher

[11] Patent Number: 6,113,566
[45] Date of Patent: Sep. 5, 2000

[54] ULTRAVIOLET BLOOD IRRADIATION METHOD AND APPARATUS

[75] Inventor: Carl Schleicher, Silver Spring, Md.

[73] Assignee: Foundation for Blood Irradiation Inc., Silver Spring, Md.

[21] Appl. No.: 09/210,947

[22] Filed: Dec. 15, 1998

[51] Int. Cl.⁷ .................................................. A61M 37/00
[52] U.S. Cl. ................................................ 604/4; 607/92
[58] Field of Search .......................... 604/4; 607/88–94; 250/432 R, 455.11, 435, 436, 437, 438; 422/24, 44

[56] References Cited

U.S. PATENT DOCUMENTS

| | | |
|---|---|---|
| 1,200,940 | 10/1916 | Henri et al. . |
| 1,683,877 | 9/1928 | Edblom et al. . |
| 2,074,909 | 3/1937 | Herzig et al. . |
| 2,308,516 | 1/1943 | Knott . |
| 2,309,124 | 1/1943 | Knott . |
| 3,926,556 | 12/1975 | Boucher ................................... 21/54 R |
| 4,321,919 | 3/1982 | Edelson . |
| 4,398,906 | 8/1983 | Edelson . |
| 4,428,744 | 1/1984 | Edelson . |
| 4,464,166 | 8/1984 | Edelson . |
| 4,612,007 | 9/1986 | Edelson . |
| 4,613,322 | 9/1986 | Edelson . |
| 4,683,889 | 8/1987 | Edelson . |
| 4,684,521 | 8/1987 | Edelson . |
| 4,737,140 | 4/1988 | Lee et al. ..................................... 604/4 |
| 5,150,705 | 9/1992 | Stinson . |
| 5,263,925 | 11/1993 | Gilmore et al. . |
| 5,290,221 | 3/1994 | Wolf, Jr. et al. . |
| 5,429,594 | 7/1995 | Castle . |
| 5,433,738 | 7/1995 | Stinson . |

Primary Examiner—Wynn Wood Coggins
Assistant Examiner—Manuel Mendez
Attorney, Agent, or Firm—Laubscher & Laubscher; R. J. Lasker

[57] ABSTRACT

Ultraviolet (UV) blood irradiation apparatus for the in vitro irradiation of blood wherein an irradiation station receives blood and irradiates blood passing through the station and a substantially planar, tube-like, elliptically-shaped body made of a material that transmits UV wavelengths in the range of 2,000 and 12,000 angstroms and an input and an output port at opposite ends thereof for respectively inputing and outputing blood, respectively; a UV source generating a low heat output whereby the irradiation station does not require cooling; a peristaltic pump receiving blood from an animal or human and pumping it through the irradiation station and returning the blood to the animal or human after passage through the irradiation station; power control switches for respectively turning power on/off from a source of electric power, and electrically connected to the pump and the source for activating/deactivating the pump and the UV source, respectively; a housing in which the irradiation station, pump and power control switches are mounted and including a movable cover for covering and uncovering the pump and the irradiation station; and sensors for monitoring the UV intensity, pump motor speed, blood flow rate and inputing data representative thereof for controlling the apparatus.

19 Claims, 4 Drawing Sheets

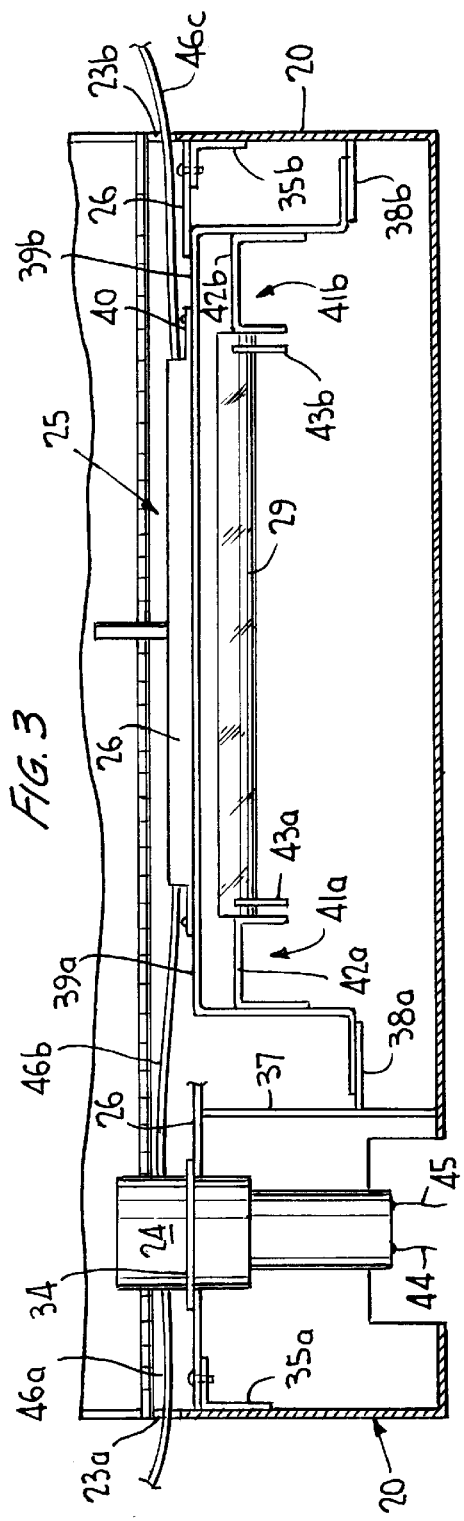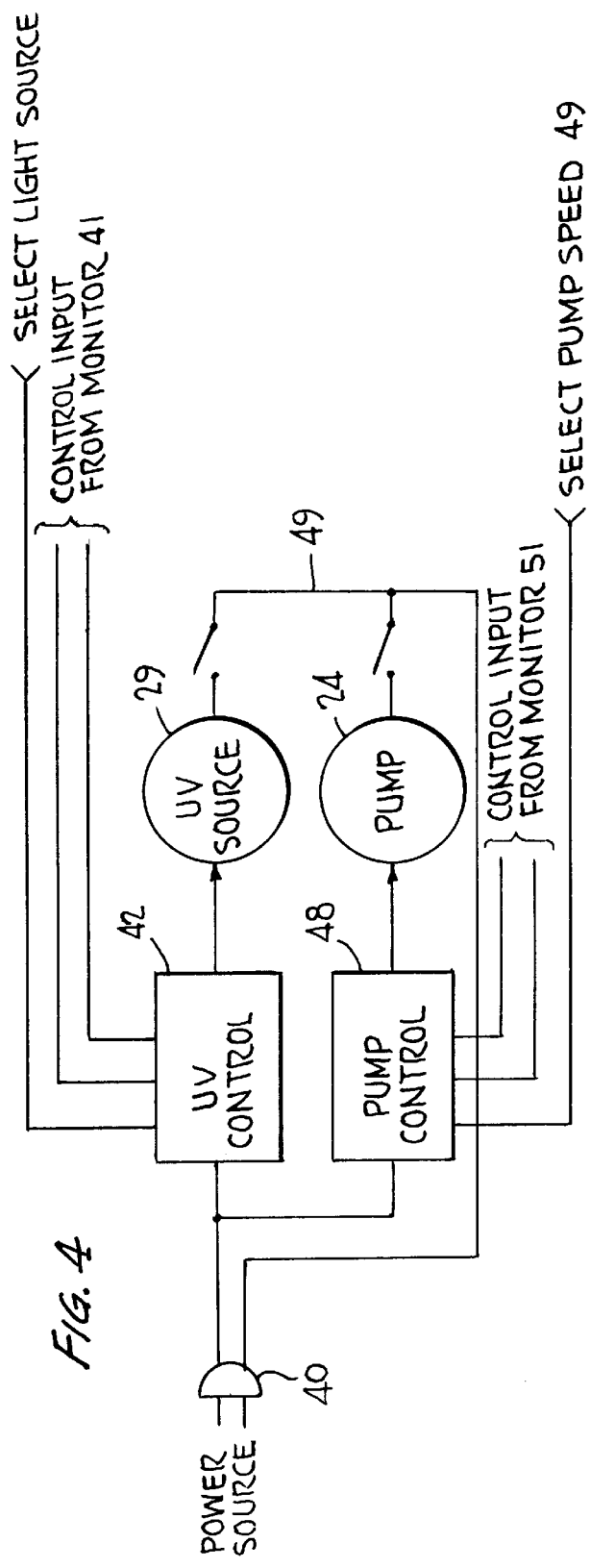

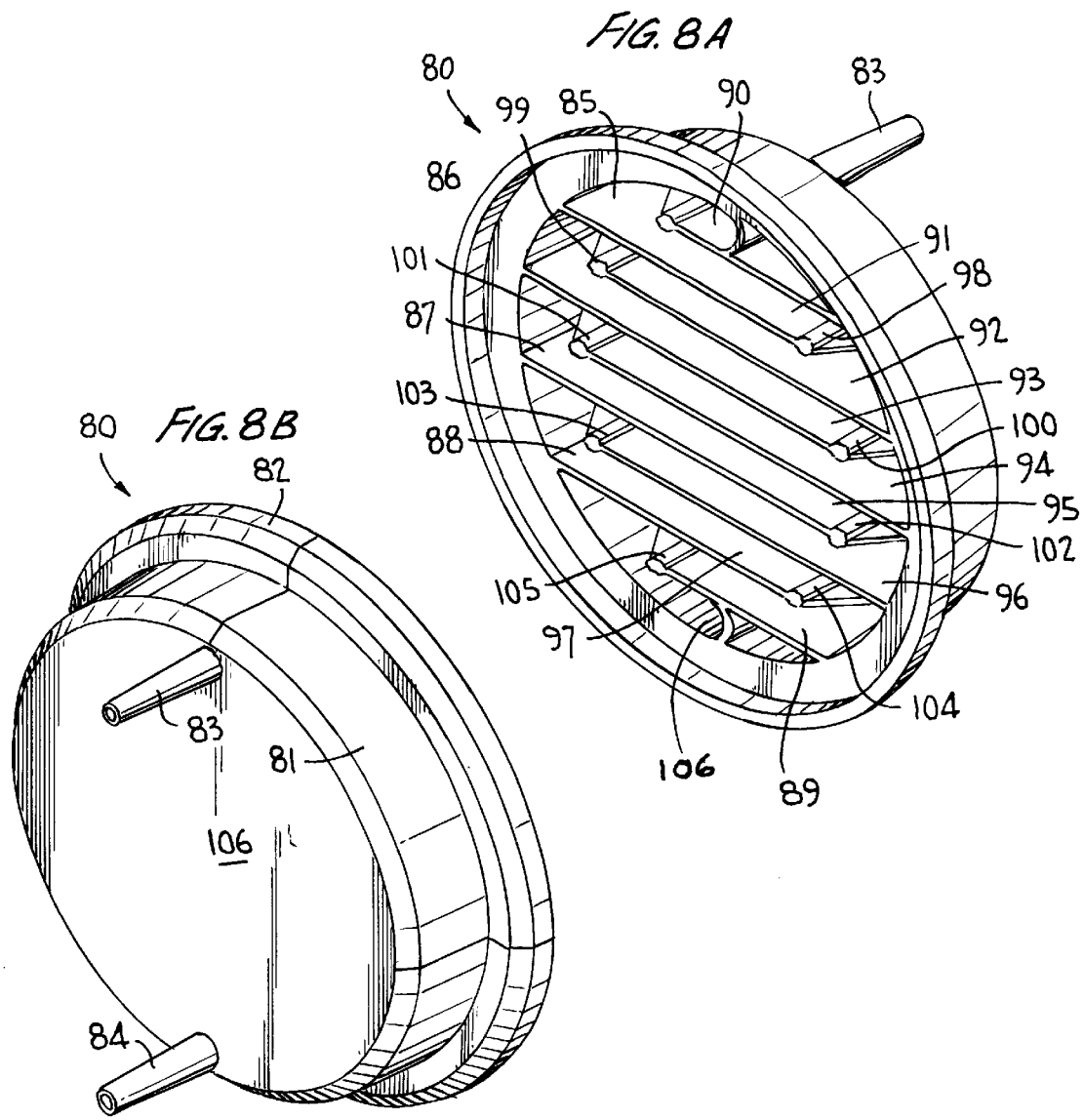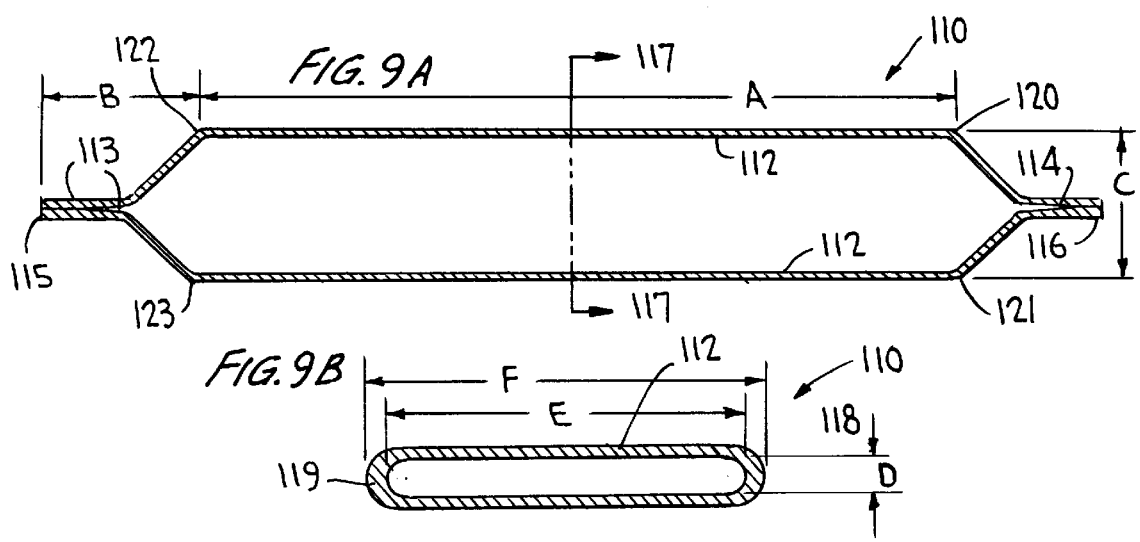

ULTRAVIOLET BLOOD IRRADIATION METHOD AND APPARATUS

BACKGROUND OF THE INVENTION

1. Field of the Invention

The invention relates to both method and apparatus for irradiating blood with ultraviolet radiation, and more particularly to such method and apparatus for in vitro radiation of blood from both humans and animals with stored blood or blood circulated outside the patient and returned to the patient after treatment.

2. Related Art

The present status of blood irradiation treatment is exemplified by the following patents.

(1) U.S. Pat. No. 1,200,940; Henri et al.; "Apparatus for treatment of Water and Other Liquids by Ultra Violet Rays: wherein water is sterilized by exposure to ultra-violet rays from a source above or within the water.

(2) U.S. Pat. No. 1,683,877; Edblom et al.; "Means for Treating Blood Stream Infections", wherein the apparatus used is a veni-puncture needle inserted into the patient's vein and the butt end of the needle is attached to tubing into which a container of citrate or oxylate solution is connected. A transfusion pump is attached to the other end of the tubing and the outlet of the pump is connected to an exposure chamber covered by a quartz lens. The source generates rays between 1800–4000 Angstroms.

(3) U.S. Pat. No. 2,074,909; Herzig et al.; "Activation Device for the Heliopyretic Treatment of Matter"; wherein a plurality of parallel radio-active penetrable tubes mounted in a frame are adapted to convey fluid to be exposed to the rays from quartz tubes and a reflector adjustable mounted in the frame to focus the rays.

(4) U.S. Pat. No. 2,308,516; Knott; "Method and Means for Irradiating Blood"; wherein a quantity of blood is removed from the patient, passed through a chamber where the blood is exposed to ultra-violet radiation for a brief, accurately controlled time and returned to said circulatory system.

(5) U.S. Pat. No. 2,309,124; Knott; "Ultra-Violet Exposure Chamber"; wherein a chambered receptacle having a series of passageways extending transversely of the chamber and a series of spirally twisted devices lie centrally of the transverse passageways to produce turbulence in the blood flow through the chambered receptacle.

(6) U.S. Pat. No. 4,321,919; Edelson; "Method and Apparatus for Externally Treating Human Blood"; wherein in a method for reducing the lymphocyte population by withdrawing blood from the subject, flowing the blood stream through a treatment station transparent to UV radiation and irradiating the blood stream in the treatment station with UV radiation in the presence of about 1 nanogram to micrograms of a dissolved psoralen capable of bonding the psoralen and the lymphocytes.

(7) U.S. Pat. No. 4,398,906; Edelson; "Method of Externally Treating the Blood"; wherein the functioning population of nucleated cells in the blood supply of a human subject by withdrawing blood from the subject and irradiating the withdrawn blood with UV radiation in the presence of an effective amount of a dissolved chemical agent having an affinity for the nucleic acid of the nucleated blood cells to form photo-adducts with DNA to thereby effect chemical bonding between the photoactive chemical agent and the nucleic acid of the nucleated cells.

(8) U.S. Pat. No. 4,464,166; Edelson; "Method for Externally Treating the Blood"; wherein the functioning population of a nucleated cell in the blood supply of a human subject by withdrawing blood from the subject and irradiating the withdrawn blood with UV radiation in the presence of a dissolved photoactivated antibody specific for the nucleated blood cell to form photoadducts with the nucleated blood cells to thereby effect chemical bonding between the photoactivated antibody and the nucleated cells.

(9) U.S. Pat. No. 4,612,007; Edelson; "Method and System for Externally Treating the Blood"; wherein the functioning population of a blood constituent in the blood supply of a human subject by irradiating withdrawn blood by UV radiation in the presence of an effective amount of a dissolved photoactive chemical agent specific for a receptor site in the blood constituent and capable when activated by UV radiation of forming photo-adducts with blood constituent receptor sites, to thereby effect chemical bonding between the photoactivated chemical agent and the receptor sites.

(10) U.S. Pat. No. 4,613,322; Edelson; "Method and System for Externally Treating the Blood"; wherein the functioning population of a blood constituent in the blood supply of a human subject is reduced by treating withdrawn blood by subjecting it to a density gradient to effect a substantial separation of the red blood cells from the blood constituent sought to be reduced in population and irradiating the treated blood with UV radiation so that the radiation impinges upon the constituent in the presence of an effective amount of a dissolved photoactive chemical agent specific and capable when activated by the UV radiation of forming photo-adducts with blood constituent receptor sites, to thereby effect chemical bonding between the photoactivated chemical agent and the receptor sites.

(11) U.S. Pat. No. 4,683,889; Edelson; "Method and System for Externally Treating the Blood"; wherein in a system for treating blood from a subject to reduce the functioning population of a blood constituent by associating and reacting the constituent with a photoactive agent including means for receiving blood and subjecting it to a density gradient for separating red blood cells from the blood constituents, and preferentially impinging UV radiation upon the blood constituent to react an associated photoactive agent with the blood constituent.

(12) U.S. Pat. No. 4,684,521; Edelson; "Method and System for Externally Treating the Blood"; wherein a chemical agent that is useful for reducing the population of a selected blood constituent having receptor sites comprises a carrier having a strong affinity for the receptor sites on or in the selected blood constituents and a photoactive agent physically incorporated within or chemically bound to the carrier moiety to interfere with the metabolism of the selected blood constituent when activated with UV radiation.

(13) U.S. Pat. No. 4,737,140; Lee et al.; "Irradiation Chamber for Photoactivation Patient Treatment System"; wherein a removable UV light ray assembly for use in a photoactivatable agent, patient treating system wherein photoactivatable agents in contact with patient blood cells are irradiated extracorporeally and then returned to the patient.

(14) U.S. Pat. No. 5,150,705; Stinson; "Apparatus and Method for Irradiating Cells"; wherein an apparatus for irradiating cells with UV light includes a UV light source and an outer cylinder surrounding the UV light source with a hollow tubing wrapped around the outer peripheral surface of the outer cylinder whereby suspended cells are transported within the hollow tubing so that the cells can be irradiated by the UV light source.

(15) U.S. Pat. No. 5,263,925; Gilmore, Jr. et al.; "Photopheresis Blood Treatment"; wherein portable apparatus is worn by the patient and blood circulating within a treatment station is irradiated with rays with continuous blood flow through the treatment station in a closed loop path.

(16) U.S. Pat. No. 5,290,221; Wolf, Jr. et al.; "Systems for Eradicating Contaminants Using Photoactive Materials in Fluids Like Blood"; wherein the blood is constricted into a relatively narrow, arcuately shaped flow path into a radiation chamber that directs radiation from one or more sources into the blood.

(17) U.S. Pat. No. 5,429,594; Castle; "Extra-Corporeal Blood Access, Sensing and Radiation Methods and Apparatuses"; wherein blood is treated with radiation in a system in which an apparatus includes one or more access ports in tubing through which blood flows with treatment and/or analysis windows disposed adjacent, within or over the ports.

(18) U.S. Pat. No. 5,433,738; Stinson; "Method for Irradiating Cells"; wherein a method for irradiating cells with UV light includes a UV light source and an outer cylinder surrounding the UV light source with a hollow tubing wrapped around the outer peripheral surface of the outer cylinder whereby suspended cells are transported within the hollow tubing so that the cells can be irradiated by the UV light source. An inner cylinder can be positioned inside the outer cylinder between the UV light source and the outer cylinder and ventilating means may be employed to maintain a substantially constant temperature.

Notwithstanding the advances made in blood irradiation as represented by the foregoing U.S. patents, there is a need for improvements in at least the cuvette employed in the irradiation stations, the manner of housing the pump and irradiation station and improving the availabe range of UV wavelength output to the irradiation station from the UV light source.

SUMMARY OF THE INVENTION

Ultraviolet (UV) blood irradiation (UBI) therapy may be administered by a device called a Knott HEMO-IRRADIATOR®, for example as disclosed in Knott's U.S. Pat. No. 2,308,516 identified above under paragraph (4). UBI therapy raises the resistance of the host and is therefore able to control many disease processes. A fundamental effect of UBI is to energize or enhance the biochemical and physiological defenses of the body by the introduction of UV energy into the blood stream. It is well known that UV radiation is used to purify water and treat sewage. It has been amply demonstrated, as evidenced by the above cited patents, that UV radiation can purify and clean the blood of contaminations in the form of viruses and bacteria.

Such treatment is intravenously applied by irradiating blood with a controlled amount of UV energy in the accepted therapeutic band. This produces a rapid detoxifying effect with subsidence of toxic symptoms. Venous oxygen is increased in patients with depressed blood oxygen values. Of special interest is that a rapid rise in resistance to acute or chronic viral and bacterial infection occurs. No harmful affects have been observed with UBI therapy in thousands of cases of viral infections, hepatitis, bacterial infections, hypoxemia and many other illnesses, especially blood-related infections.

The diseases successfully treated with UBI include: (1) Atypical pneumonia; (2) Poliomyelitis and polioencephalitis; (3) Hepatitis; infectious and serum; (4) Influenza; (5) common upper respiratory disease; (6) Herpes simplex; (7) Herpes zoster; (8) Mumps; (9) Mononucleosis; and (10) measles.

Moreover, preliminary reports indicate that UBI may be useful in treating HIV and research is currently under way to evaluate the effects of UBI on eliminating HIV from blood and blood products. If this research is successful, it would have major implications in ensuring the safety of blood in blood banks.

The Knott technique of blood irradiation (approved by the American Blood Irradiation Society) has achieved the following physiologic objectives: (1) increases the blood oxygen level; (2) increases phagocytosis; (3) relieves toxemia; (4) decreases edema; and (5) controls nausea and vomiting.

Treatment generally consists of withdrawing from 1.0 to 1.5 cc of blood per pound of body weight from the patient, citrating it and, by use of the Knott HEMO-IRRADIATOR® exposing it to radiant energy between the wave lengths of 2,000 and 12,000 angstroms units as it passes through the irradiation unit at a predetermined flow rate. The blood is returned to the patient through the needle used for the initial venipuncture. Treatment requires from 30–45 minutes. Outpatients rest fifteen minutes, after which time they may resume whatever activity is permitted.

The primary object of the present invention is to provide an improved blood irradiation method and apparatus based on the aforementioned Knott-HEMO-IRRADIATOR® device which has FDA approval.

Other objects, advantages and features of the present invention are to: (1) provide a pump and UV light source interface that enables the UV light source to be changed without disassembling the pump; (2) provide solid state electronic circuitry thereby eliminating the use of vacuum tubes; (3) provide a counter to record the number of exposure sessions, thereby making available a usage history and assist in billing patients; (4) incorporate power circuitry to allow both international and domestic use; (5) use a UV radiation source which emits relatively little heat during usage, thus eliminating the need for a cooling system and also allowing the use of polymeric materials; (6) incorporate a self-diagnostic capability to monitor the pump, UV source and control system; (7) provide the ability to select the type of UV range, i.e. UVA, UVB or UVC; (6) incorporate a data output port for printer, floppy drive, hard drive, etc.; (9) significantly reduce the size and weight of the apparatus for easier portability of the apparatus; (10) use a clear polymeric irradiation chamber, preconnected to the disposable IV set; (11) provide use of a material for use as a cuvette for irradiating blood and which is equivalent to quartz crystal in the transfer of UV to the irradiated blood for inactivation of pathogens in the blood; (12) to provide disposable cuvettes; (13) provide total containment of the UV source and irradiation chamber to prevent leakage of UV energy into the environment and include a cover shield for shielding the eyes of the operator while enabling observation of the blood flow through the cuvette in the irradiation station; (14) a UV blood irradiation apparatus that fully complies with the safety regulations of OSHA and other government regulatory agencies and to incorporate sensors to monitor UV intensity motor speed, blood flow rate, etc.; (15) provide intermittent operation of the UV source coupled with providing turbulent blood flow within irradiation chamber; (16) to provide various wavelengths in the range from 2,000 to 12,000 Angstroms for the irradiation treatment of blood; (17) enable improved quality control of the control circuitry for controlling the pump and the UV light source; and (18) provide apparatus of the type specified herein that is user friendly to the average nurse or technician by providing standardized IV sets.

BRIEF DESCRIPTION OF THE DRAWINGS

The above objects, features and advantages of the invention are believed to be readily apparent from the following description of a preferred embodiment representing the best mode for carrying out the invention when taken in conjunction with the following drawings, wherein:

FIG. 3 is a cross section view taken along lines 3—3 of FIG. 2 and illustrating the mounting of the pump and irradiation station;

FIG. 4 is a block diagram of the control circuitry for the pump and the UV light source;

FIGS. 8A and 8B respectively illustrate front and rear perspective views of a first embodiment of an irradiation cuvette for irradiating blood flowing therethrough when the cuvette is inserted into the irradiation chamber and which is designed to create turbulence in the blood flow; and FIGS. 9A and 9B illustrate a second embodiment of an irradiation cuvette for irradiating blood flowing therethrough when the cuvette is inserted into the irradiation chamber and which is thin to prevent blockage of the UV irradiation by the blood flow.

DETAILED DESCRIPTION

Figure 1:
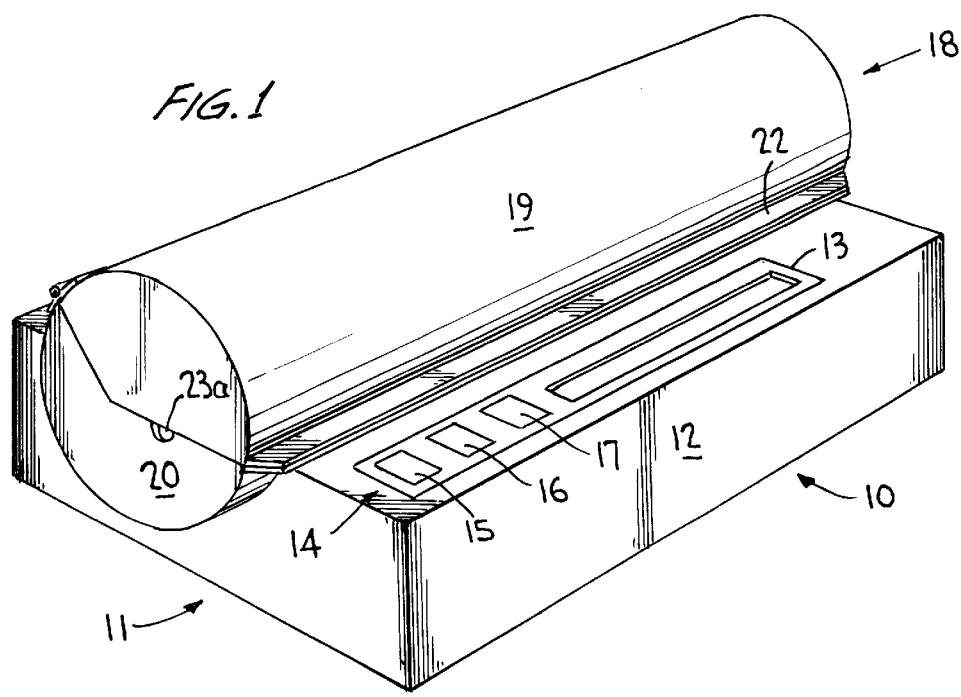
FIG. 1 illustrates a top perspective view of the UV blood irradiator apparatus of the preferred embodiment of the invention with the top cover closed as it would be during excitation of the UV light source or non-use of the irradiating apparatus.

With reference to the perspective view of the irradiation apparatus of the invention as shown in FIG. 1, the blood irradiation apparatus 10 includes a front panel 12 with a display 13 and power control switches 14 comprising ON/OFF main power switch 15, ON/OFF pump control switch 16 and ON/OFF UV light control switch 17, thereby providing separate power control to the irradiation device 10 itself as well as separate power control of the pump and UV light source (both components not shown in FIG. 1).

Figure 2:
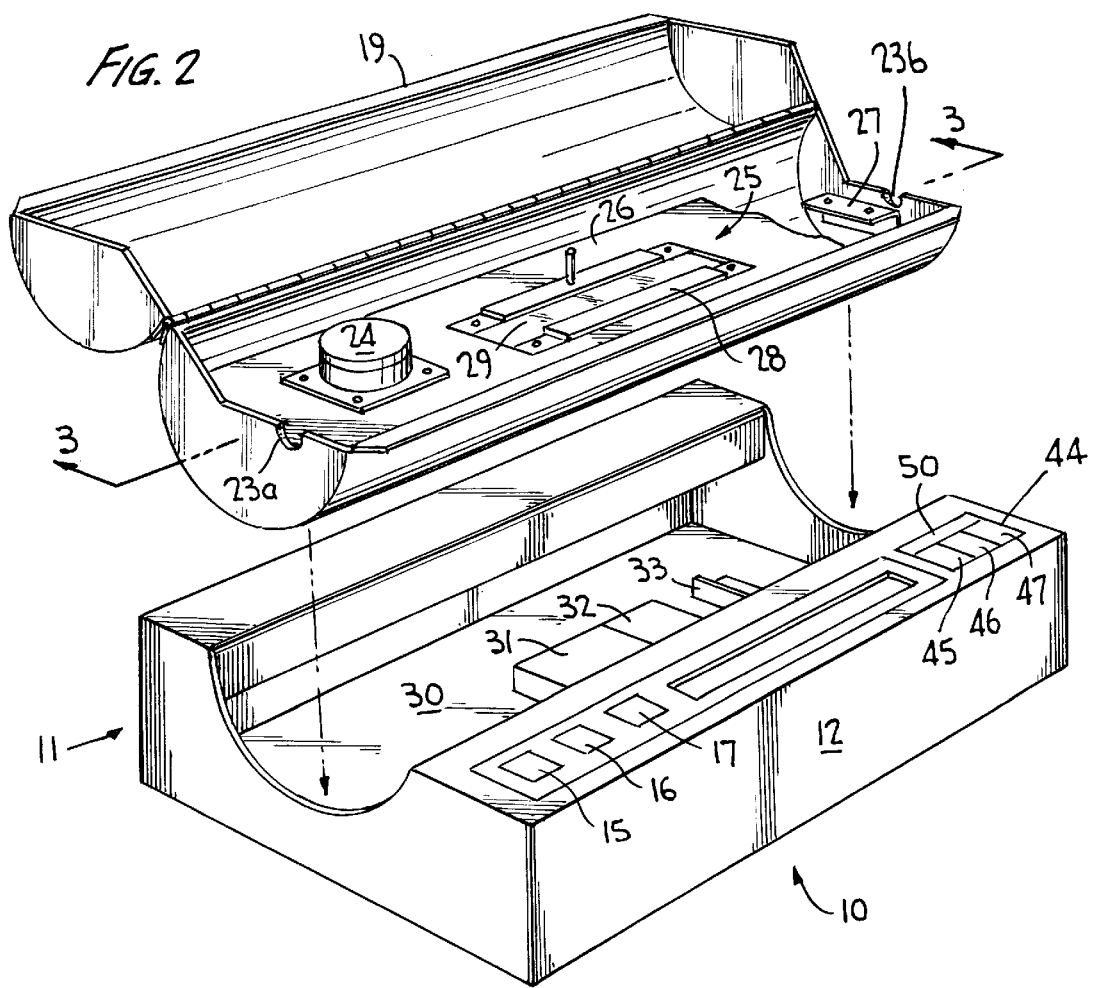
FIG. 2 illustrates the top perspective view of the invention of FIG. 1 with the cover, pump and irradiation station assembly in an exploded view, illustrating the inside of the irradiation apparatus housing.

The housing 11 of the blood irradiation apparatus 10 further comprises a tubular housing 18 with a partially rotatable cover 19 opening to the rear of the housing 10 as shown in FIG. 2. Section 20 of housing 18 is secured in the body of housing 11 as illustrated in FIG. 1. Lip 21 of section 20 and lip 22 of rotatable cover 19 are closed on one another with cover 19 in a closed position as illustrated in FIG. 1. Rotatable cover 19 may be made of metal or, in a preferred embodiment of the invention, of UV plastic. UV plastic is lighter than metal, and enables the operator of the blood irradiator apparatus of the invention to observe the flow of blood through a cuvette (to be described with respect to FIG. 2) in an irradiation station 25 (FIG. 2) located beneath cover 19. Aperture 23a in section 20 provides egress for the conduit transporting the blood from the patient to the pump 24 (FIG. 2).

Housing 10 and the various structural components described above are preferably made from metal similar to that used for storage cabinets.

The exploded perspective view of the blood irradiator apparatus of FIG. 2 illustrates the relationship between the blood pump 24 and the irradiation station 25. A cover plate 26 (shown in FIG. 3) is removed in FIG. 2 to more clearly illustrate the pump and the irradiation station. Brackets 35a and 35b support respective opposite ends of the cover plate 26 as shown in FIG. 3.

Blood from the patient is transported via a conduit (see FIG. 3) through aperture 23a to the pump 24 and thence to a cuvette (not shown) mounted in irradiation station 25 by brackets 26, 28, thereby enabling blood flowing through the cuvette to be irradiated by the UV light from UV light source 29. Blood from the cuvette is then transported via a conduit (see FIG. 3) through aperture 23b and returned to the patient by means well known to those skilled in the blood irradiation art.

With cover 19 in the open position as illustrated in FIG. 2, access is provided to the pump 24 and the irradiation station for purposes of removing or servicing these components, for example to change the UV light source 29 or replace and position the cuvette in brackets 26, 28 of the irradiation station 25.

The lower section 30 of housing 11 provides space for mounting the electrical components of the blood irradiation apparatus 10. Such components are illustrated by block components 31, 32 and 33. The manner in which such electrical components are stored in lower section 30 forms no part of the present invention as one of ordinary skill in the blood irradiation art would readily perceive the location of such components in order to carry out the invention.

The cross section view of FIG. 3 shows the manner in which the pump 24 and the irradiation station 25 including UV light source 29 are mounted in lower section 20 of tubular housing 18. Shoulder 34 of pump 24 rests on cover plate 26 and is secured thereto by fastening means such as machine screws (not shown) and cover plate 26 in turn is secured to bracket 35a attached to the side of lower section 20. Cover plate 26 is similarly secured to bracket 35b at the other end of lower section 20. Cover plate 26 rests on support 37 which includes protrusion 38a for supporting support member 39a upon which is secured one end of bracket 26 of the irradiation station 25. Similarly the other end of cover plate 26 is supported on support member 39b which is secured to protrusion 38b. The other end of bracket 26 of the irradiation station is secured to support member 39b by fastening means 40 as shown in FIG. 3.

UV light source 29 is removably retained at each end by respective holding elements 41a, 41b, each of which comprises a support 42a and 42b having respective sockets 43a and 43b. Electrical power is supplied to pump 24 via electrical conductors 44, 45. The electrical conductors for supplying power to the UV light source 29 are not shown in FIG. 3.

Tube 46a conveys blood from the human or animal patient to the pump 24; tube 46b conveys blood from pump 24 to the cuvette in irradiation station 25; and tube 46c returns blood from the irradiation station 25 to the human or animal patient (not shown).

The control circuitry 49 for controlling the UV light source 29 and the pump 24 is shown in block diagrammatic format in FIG. 4, wherein both the UV light source 29 and pump 24 receive power through respective ON/OFF power switches 16 and 17 from power source 40. In a preferred embodiment of the invention, UV light source 29 is one of several UV light sources, each one providing a UV light output having an appropriate bandwidth to cover the respective UVA, UVB and UVC wavelengths. Control input signals 41 from a diagnostic monitor (to be described with respect to FIG. 7) are input to UV control circuitry 42 so that the particular UV light source 29 maintains the proper light output amplitude (wattage).

In a further modification of the present invention, a broad band UV light source such as a quartz lamp known to the art serves as the UV light source 29, and various filters each having a different light transmission bandwidth, for example for each of the UVA, UVB and UVC light bandwidths) are inserted within bracket 26 of irradiation station 25 (FIG. 2) to be positioned between the UV light source 29 and the cuvette through which the blood is pumped in the irradiation station. In this modified embodiment of the invention a select light source signal 43 from a control panel 44, having, for example, three selector switches 45, 46 and 47, on front panel 12 of the HEMO-IRRADIATOR® apparatus 11 of the invention (FIG. 1) provides a control input to UV control circuitry 42 to properly control the excitation to the UV light source to obtain the desired UV light output amplitude in accordance with the UV light source that is selected.

In general it is possible to vary the light source intensity by changing either the voltage or current of a light source and thereby vary its radiant output. With incandescent sources such variation can extend over a wide range. With arc sources the range of variation is narrower since the arc can not be allowed to extinguish or the UV treatment will fail. The frequency output wavelengths can be adjusted by using filters or changing the UV light source.

In a similar manner pump control circuitry 48 is powered from mains power source 40 and receives a select pump speed signal 49 from pump speed select switch 50 mounted on front panel 12 of the HEMO-IRRADIATOR® apparatus 10 illustrated in FIG. 2. Speed select switch may comprise a rotatable potentiometer switch to provide a continuum of pump speeds. It is known that it is desirable that the blood flow through the cuvette in the irradiator station 25 be varied in accordance with the type of cuvette being used and the UV light output amplitude from the UV light source.

For various physiological and/or operational reasons it may be desirable to increase/decrease the blood flow rate. In the apparatus of the present invention this variation in the blood flow rate is provided as a manual operation (see FIG. 4) As illustrated therein, there are two inputs, namely light source 48 and pump speed 49. These inputs are reference inputs which are varied manually to obtain the desired blood flow rate and/or radiation level.

Figure 6:
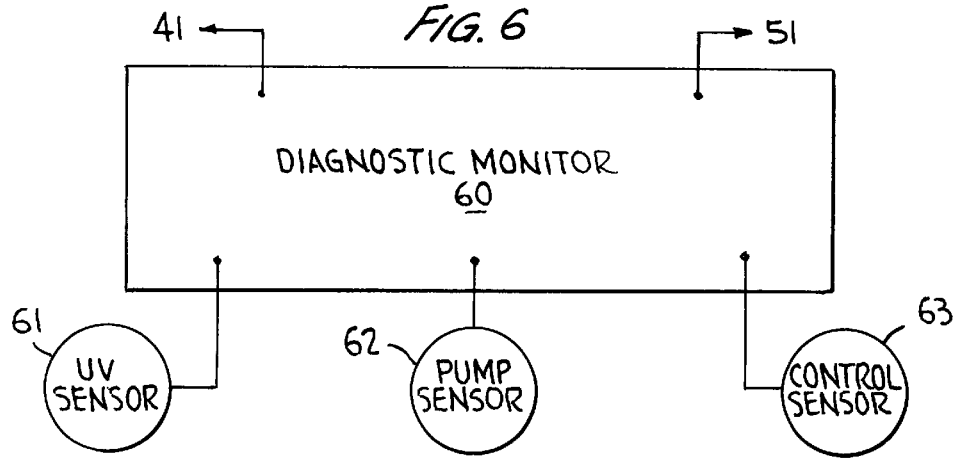
FIG. 6 shows a diagnostic monitor for receiving diagnostic inputs from the UV light source, pump control, UV light source, pump and control sensors and for providing control input signals to the control circuitry of FIG. 4.

Pump control circuitry also receives control input signals 51 from the diagnostic monitor 60 (to be more fully described with respect to FIG. 6).

Figure 5:
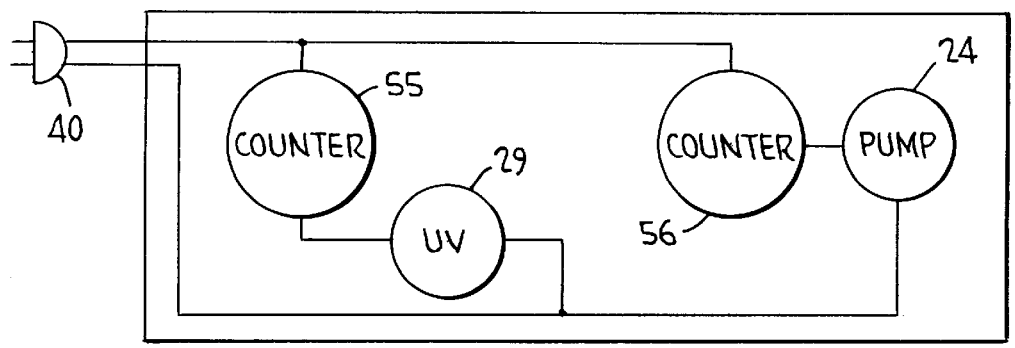
FIG. 5 is a block diagrammatic representation of the circuitry for sensing current flow to the UV light source and the pump.

In HEMO-IRRADIATOR® apparatus of the type disclosed herein it is desirable to determine the usage of the pump 24 and UV light source 29 so that, for example, the pump may be removed for necessary maintenance and the anticipated need for replacing the UV light source 29 anticipated as it approaches its specified life cycle. To that end FIG. 5 illustrates the use of counters 55 and 56 which are respectively sensing the current flow to UV light source 29 and pump 24.

UV light source sensor 61 and pump sensor 62 each respectively sense the current and/or voltage of the UV light source 29 and the pump 24, respectively. These analog signals may be converted by A/D converters and then respectively compared with stored values in, for example a ROM, in diagnostic monitor 60. Differences between the sensed current and/or voltages and the stored values provide respective control signals 41 and 51 to the respective UV control circuitry 42 and the pump control circuitry 48 of FIG. 4.

Thus, diagnostic monitor 60 senses the operation of the pump control circuit 48 and the UV control circuit 42 of FIG. 4 to determine if the control circuitry is working. This is important as improper operation of the control circuitry results in a failed UV blood irradiator treatment.

Figure 7:
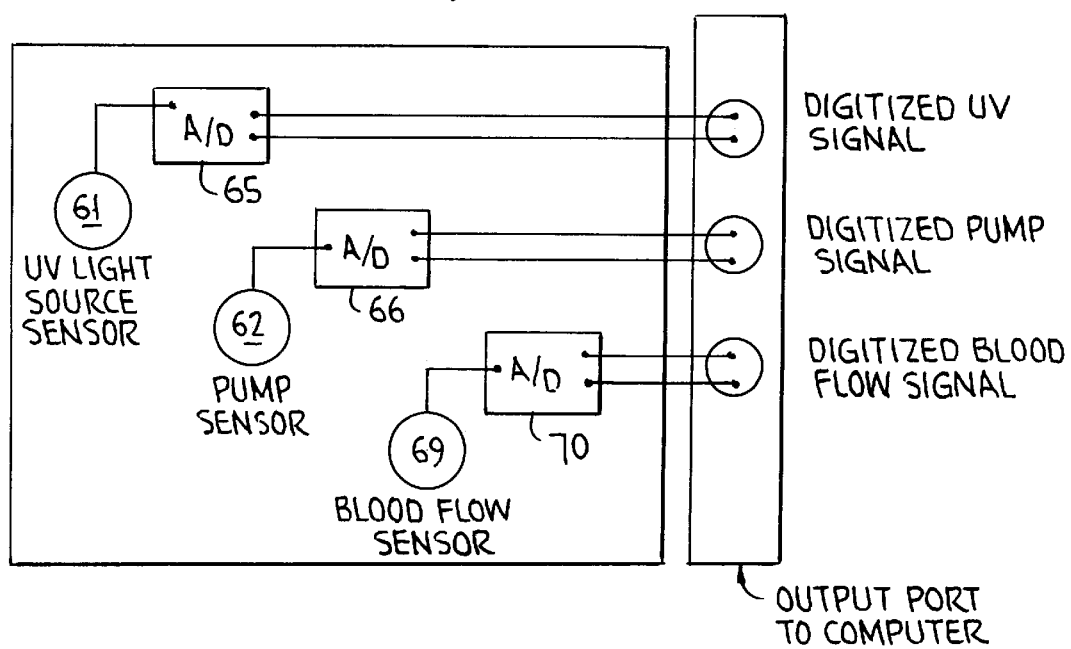
FIG. 7 shows the digital output ports for providing digitized UV light source, pump and blood flow signals as generated by A/D conversion of the respective outputs of the UV light source, pump and blood flow sensors.

FIG. 7 shows the digital output ports for providing digitized UV light source, pump and blood flow signals as generated by A/D conversion of the respective outputs of the UV light source, pump and blood flow sensors, which digitized data may be provided at suitable ports located on the back of the HEMO-IRRADIATOR® apparatus (not shown) for transmission via modems by telephone and/or cable to remote locations. Thus the respective outputs of UV light source sensor 61 and pump sensor 62 are converted by A/D converters 65 and 66 and their respective digital outputs are provided to digital output ports. In a similar manner, the output of blood flow sensor 69 is converted by A/D converter 70 and provided as a digitized output at digital port 71.

FIG. 8A is a front perspective view of first embodiment of a cuvette 80 capable of being used in the irradiation station 25 (FIG. 2) of the blood irradiation apparatus of the subject invention and which requires a modification of the irradiation station to accommodate the cuvette therein, which modification will be described hereinafter. Cuvette 80 may have an elliptical or oval shape comprising a main body portion 81 and a lip 82 extending around the periphery of body portion 81. Lip 82 provides a means for fastening cuvette 80 in irradiation station 25 (described hereinafter). Blood flows into cuvette 80 via inlet 83 and flows from the cuvette via outlet 84 (see FIG. 8B).

The interior of cuvette 80 comprises a number of parallely-spaced chambers 85, 86, 87, 88 and 89 through which blood successively flows in alternate directions (as indicated by the directional arrows in FIG. 8A) from inlet 83 and entry port 90 to outlet port 91 and then from cuvette 80 via outlet 84. The blood flows through chambers 85, 86, 87, 88 and 89 within respective channels 90, 91, 92, 93, 94, 95, 96 and 97. Each of the channels includes a respective diverter 98, 99, 100, 101, 102, 103, 104 and 105 located at the end of each channel in the direction of the blood flow and each of which interrupts the flow of blood and causes it to drop onto an adjacent channel.

The above-described construction of cuvette 80 causes the blood flow therein to be turbulent, thereby eliminating the tendency of the blood to coagulate and also providing an appropriate exposure of the blood from the UV source (not shown) but which irradiates the blood through a quartz or polymeric facing which covers the interior of the cuvette 80.

The rear view of cuvette 80 shown in FIG. 8B illustrates back cover 106, main body portion 81, lip 82 and the spaced relationship of blood inlet 83 and blood outlet 84.

The second embodiment of a cuvette illustrated in FIGS. 9A and 9B is a preferred embodiment of the invention and may be disposable to eliminate the contamination of blood from one blood sample to the next. Cuvette 110 is an elongated hollow tube 112 having an oval-shaped cross-section as illustrated in FIG. 9B and which includes a necked-down portion 113 and 114 at the blood inlet 115 and blood outlet 116, respectively, thereby diverting the blood flow into the respective upper and lower halves of hollow tube 112 as shown in FIG. 9A. The Hollow tube section A shown in FIG. 9A is approximately 5.0" long, 1.0" wide (Dimension C), and each of inlet 115 and outlet 116 (dimension B) is approximately 1.0".

FIG. 9B is a sectional view of the cuvette 110 taken along lines 117—117 of FIG. 9A. As illustrated in FIG. 9B, hollow tube 112 has inner spacing (dimension D) of approximately 0.85", an inner width of 0.837" (dimension E) and an outer width of approximately 0.96". With the above dimensions, hollow tube 112 has a diameter of approximately 0.0615 inches (dimension F–dimension E) at the outer wall portions and a diameter of approximately 0.075" at the end portions 120, 121, 122 and 123 (dimension C–dimension D).

It is desirable that the HEMO-IRRADIATOR® apparatus of the present invention be capable of wide usage in different countries world wide and therefore it is advantageous that the power supply of the apparatus be capable of accepting both 110 and 220 volt power supply inputs and transform that voltage input to 110 volts AC, the voltage required to operate the apparatus of the invention. Those of ordinary skill in the art of power supplies will readily recognize that such power transformers are available for use in the present invention, such that no further description of their operation is necessary for the present invention to be practiced.

The above description serves only to describe exemplary embodiments of the best mode of making the HEMO-IRRADIATOR® apparatus of the invention and to demonstrate the features and advantages of its construction and operation. The invention is not intended to be limited thereby, as those skilled in the hemo-irradiator art will readily perceive modifications of the above-described embodiments. Thus the invention is intended to be limited only by the following claims and the equivalents to which the claimed components thereof are entitled.

What is claimed is:

1. Ultraviolet (UV) blood irradiation apparatus for the in vitro irradiation of blood, comprising:

an irradiation station for receiving blood and including a source of UV radiation for irradiating blood passing through the station and including a substantially planar, tube-like, hollow, elliptically-shaped body made of a material that transmits UV wavelengths in the range of 2,000 and 12,000 angstroms and having an input and an output port at opposite ends thereof for respectively inputing blood and outputing blood into and out of said tube-like body, respectively;

said source providing a range of wavelength output from 2000 to 12,000 angstroms and generating a low heat output whereby the irradiation station does not require cooling;

a peristaltic pump for receiving blood from an animal or human and pumping it through said irradiation station and returning the blood to the animal or human after passage through the irradiation station;

power control switches for respectively turning power on/off from a source of electric power, and electrically connected to the pump and the source for activating/deactivating the pump and the source, respectively;

a housing in which said irradiation station, pump and power control switches are mounted and including a movable cover for covering and uncovering the pump and the irradiation station;

means for controlling the operation of the pump and the UV source; and sensors for monitoring the UV intensity, pump motor speed, blood flow rate and inputing data representative thereof into said means for controlling.

2. Ultraviolet (UV) blood irradiation apparatus as claimed in claim 1, wherein each irradiation of blood is a separate exposure session and further comprising a counter for recording the number of exposure sessions.

3. Ultraviolet (UV) blood irradiation apparatus as claimed in claim 1, wherein the source of electric power is adapted to both domestic and international power mains.

4. Ultraviolet (UV) blood irradiation apparatus as claimed in claim 1, further comprising self-diagnostic circuitry for monitoring said pump, UV source and control system and providing diagnostic control signals to said means for controlling to correct errors in the operation of the irradiation apparatus.

5. Ultraviolet (UV) blood irradiation apparatus as claimed in claim 1, wherein said means for controlling further including UV filters and a cuvette, each UV filter being interposed between the UV source and the cuvette in the irradiation station and respectively providing a UV output wavelength in the range of UVA, UVB and UVC.

6. Ultraviolet (UV) blood irradiation apparatus as claimed in claim 1, wherein the source of UV radiation provides UV output wavelengths in the range of UVA, UVB and UVC.

7. Ultraviolet (UV) blood irradiation apparatus as claimed in claim 1, further comprising a data output port connected to said sensors for each of a printer, floppy drive and hard drive.

8. Ultraviolet (UV) blood irradiation apparatus as claimed in claim 1, wherein the movable cover is closed during operation of the UV source to prevent leakage of UV energy into the environment, and said means for controlling including a switch activated with opening of said cover to cause said means for controlling to deactivate said UV source to prevent leakage of UV energy into the environment.

9. Ultraviolet (UV) blood irradiation apparatus as claimed in claim 1, wherein said cover is plastic and transparent so that the blood flowing through said irradiation station may be observed.

10. Ultraviolet (UV) blood irradiation apparatus as claimed in claim 1, wherein the irradiation station further includes a cuvette affording turbulent blood flow therethrough and said means for controlling operates said UV source intermittently.

11. Ultraviolet (UV) blood irradiation apparatus as claimed in claim 1, wherein said housing is portable.

12. Ultraviolet (UV) blood irradiation apparatus as claimed in claim 4, further comprising a display means and wherein said diagnostic control signals are displayed on said means for displaying.

13. Ultraviolet (UV) blood irradiation apparatus as claimed in claim 12, further comprising sensors for monitoring the UV intensity, pump motor speed, blood flow rate and inputing data representative thereof to said display means.

14. Ultraviolet (UV) blood irradiation apparatus as claimed in claim 13, wherein the irradiation station further includes a cuvette affording turbulent blood flow therethrough and said means for controlling operates said UV source intermittently.

15. Ultraviolet (UV) blood irradiation apparatus as claimed in claim 6, wherein each irradiation of blood is a separate exposure session and further comprising a counter for recording the number of exposure sessions.

16. A disposable cuvette for the transmission of blood through a UV irradiation station, comprising:

a substantially planar, tube-like, hollow, elliptically-shaped body made of a material that transmits UV wavelengths in the range of 2,000 and 12,000 angstroms and having an input and an output port at opposite ends thereof for respectively inputing blood and outputing blood into and out of said tube-like body, respectively;

said body having separate channels digressing from said input port to said output port along the sides of said body; and said channels being dimensioned to sufficiently restrict the flow of blood therethrough to enable UV radiation of the blood.

17. A cuvette as claimed in claim 16, wherein said tube-like body has a thickness of approximately 0.06", a width of 1.0" and a separation between the channels of said body of approximately 0.95".

18. A cuvette as claimed in claim 16, wherein said body is made of special synthetic materials having UV light transmission characteristics equivalent to the UV light transmission characteristics of quartz crystal material.

19. A cuvette as claimed in claim 16, wherein said body is made of a material having equivalent radiation transfer characteristics between 2,000 to 12,000 Angstroms to that of fused silica or quartz.

* * * * *